US008670290B2

(12) United States Patent
Aklil et al.

(10) Patent No.: US 8,670,290 B2
(45) Date of Patent: Mar. 11, 2014

(54) METHOD FOR DETERMINING THE LOCATION OF AN IMPACT ON A SURFACE OF AN OBJECT

(75) Inventors: Djamel Aklil, Marseilles (FR); Thomas Fillon, Savigny-sur-Orge (FR)

(73) Assignee: Elo Touch Solutions, Inc., Milpitas, CA (US)

( * ) Notice: Subject to any disclaimer, the term of this patent is extended or adjusted under 35 U.S.C. 154(b) by 499 days.

(21) Appl. No.: 12/991,419

(22) PCT Filed: Apr. 21, 2009

(86) PCT No.: PCT/EP2009/002903
§ 371 (c)(1),
(2), (4) Date: Jun. 27, 2011

(87) PCT Pub. No.: WO2009/135589
PCT Pub. Date: Nov. 12, 2009

(65) Prior Publication Data
US 2011/0261655 A1    Oct. 27, 2011

(30) Foreign Application Priority Data
May 7, 2008   (EP) .................................. 08290430

(51) Int. Cl.
*G01S 3/80*        (2006.01)
(52) U.S. Cl.
USPC ............................ 367/125; 367/900; 367/902
(58) Field of Classification Search
USPC ............. 367/125, 907, 900; 178/18.04, 19.02
See application file for complete search history.

(56) References Cited

U.S. PATENT DOCUMENTS

| 2004/0173389 A1 | 9/2004 | Sullivan | |
| 2011/0261655 A1 * | 10/2011 | Aklil et al. | 367/125 |

FOREIGN PATENT DOCUMENTS

| CN | 101071357 A | 11/2007 | |
| EP | 2116921 A1 * | 11/2009 | G06F 3/043 |
| JP | 62017677 A | 1/1987 | |
| JP | 2004534329 | 11/2004 | |
| JP | 2005260781 A | 9/2005 | |
| JP | 2009271045 A * | 11/2009 | |
| WO | WO 03/005292 A1 | 1/2003 | |
| WO | WO 2003/005292 A | 1/2003 | |
| WO | WO 2006067851 | 6/2006 | |
| WO | WO 2006/108443 A | 10/2006 | |
| WO | WO 2009135589 * | 11/2009 | G06F 3/043 |

OTHER PUBLICATIONS

May 24, 2011 Office Action (translated) from Japanese Patent Office for corresponding JP application 2008-154570.
Office Action for Chinese Application No. 200980116086.1 dated Jul. 23, 2012.
International Search Report for International Application No. PCT/EP2009/002903.

* cited by examiner

*Primary Examiner* — Daniel Pihulic
(74) *Attorney, Agent, or Firm* — Alston & Bird LLP

(57) ABSTRACT

The invention relates to a method for determining the location of an impact on a surface of an object based on the analysis of an acoustic signal generated by the impact. This method further comprises a signal treatment step of weighting the acoustic signal to take into account spurious contributions in particular due to reflections at the border of the object.

15 Claims, 8 Drawing Sheets

METHOD FOR DETERMINING THE LOCATION OF AN IMPACT ON A SURFACE OF AN OBJECT

CROSS-REFERENCE TO RELATED APPLICATIONS

The present application is the national phase entry of PCT/EP2009/002903 having international filing date Apr. 21, 2009, which claims priority to European patent application 08 290 430.1 filed May 7, 2008.

The invention relates to a method for determining the location of an impact on a surface of an object based on the analysis of an acoustic signal generated by the impact.

Such a method is known from WO 2006/108443, disclosing a method for determining the location of an impact on a surface comprising N transducers, transmitting a sensed signal $s_i(t)$ to a processing unit, wherein the method comprises the steps of: a) computing P inter-correlation products out of the Fourier transforms of the sensed signals of the N different transducers, b) calculating the inverse Fourier transforms $p'_{ij}(u)$ of the P inter-correlation products, c) computing for each area k of the surface of the object the $P_k(u) = \Sigma p_{ij}(u - \tau_{ijk})$ and d) finding the area $k_0$ for which the characterizing value of $P_{k0}(u)$ is maximum among the characterizing values $P_k(u)$ of all areas k. Here $\tau_{ijk}$ corresponds to the time difference of arrival of the signal sensed by two different transducers for each area k.

The localization method is thus based on the presence of a pronounced peak in the sum of the cross-correlation functions at the position where the impact occurred. Nevertheless, under certain circumstances, the determination of the impact location is falsified by spurious contributions arising from reflections of the acoustic signal in the border region of the object or some other discontinuities in the object, like a screw, crack or a hole.

It has been proposed to overcome this problem by cutting off the signals after a predetermined time interval or by using a low pass filter. The results obtained by the proposed solutions are, nevertheless, not satisfying. In cases where a clear separation between sensed signal received without reflections and reflected sensed signal is not possible, which, for example, can occur in case of signal dispersion due to the properties of the material, the cutting off leads to an amended signal, from which the localization accuracy of the impact is also limited.

SUMMARY OF THE INVENTION

It is therefore the object of the present invention to provide a method to treat the sensed signals to better take into account spurious contributions, like contributions from reflections at the border of the object.

This object is achieved with the method according to claim 1. By weighting the acoustic signal, it becomes possible to keep the entire information of the signal while, at the same time, amplifying the contribution from the sensed signal which is directly received from the location of the impact with respect to contributions that may arise from reflections at the border of the object and which typically arrive later. As a consequence the determination of the location of the impact becomes more stable and precise In this context, it is understood that the acoustic signal which is treated is not necessarily the signal immediately sensed by transducers but can already have been treated, e.g. by an analogue-to-digital transformation.

Preferably the weighting is carried out in the time domain, for which the best results have been achieved in identifying the location of an impact.

According to a preferred embodiment, the signal treatment step can comprise the step of identifying a first wave front of the acoustic signal and a step of applying a damping window. The acoustic signal spreads out over the object after an impact and is sensed by a certain number of transforming means, e.g. transducers. As the first reflected contribution of a signal can only be sensed after the first wave front of the acoustic signal has already reached the transducer in question—due to geometric reasons—the identification of the first wave front is a robust parameter to identify the part of the signal which should have a higher weight factor than the rest of the sensed signal and which is taken into account by the step of applying the damping window. In this context the term "first wave front" means the part of the signal which reaches the transforming means without spurious contributions from reflections.

Preferably, the step of identifying a first wave front can comprise identifying the maximum signal amplitude. The maximum signal amplitude is a parameter which is easily detectable, therefore not requiring extensive computational power and, at the same time, is a robust starting parameter for finding out the beginning of the acoustic signal. Instead of the maximum amplitude alternative parameters of the sensed acoustic signal could be the power of the signal, the maximum peak to peak amplitude or the energy of the signal. Prior to identify the signal amplitude a further step of signal rectification and smoothing can be carried out to facilitate the data analysis.

According to an advantageous embodiment, the step of identifying the first wave front furthermore comprises determining the arrival of the first wave front as the time when the acoustic signal passes a threshold value which is based on the maximum signal amplitude. For example, the arrival of the first wave front of the acoustic signal can be attributed to the time at which a certain percentage of the maximum amplitude is reached.

Preferably, the step of applying a damping window can comprise using multiplying the acoustic signal with an exponential damping window:

$$w(t) \begin{cases} = 0, & \text{for } 0, t < t_i - \Delta t \\ = \exp((t_i - \Delta t - t)/T), & \text{for } t_i - \Delta t <= t \end{cases}$$

wherein $t_i$ corresponds to the time of arrival of the first wave front and $\Delta t$, a time delay and T being the exponential time constant.

It appeared that best results in the data analysis were achieved for such an exponential damping window wherein the term $\Delta t$ ($\Delta t > 0$) is a time delay which shifts the starting of the damping window preferably to an earlier time to further optimize the result. Depending on the application, $\Delta t$ can be a fixed value or adapted, e.g. on initialization of the device.

Advantageously, the acoustic signal can be sensed by at least two transforming means, and wherein the first wave front is identified for one, in particular only one, transforming means such that the same time origin of the damping window is applied for all transforming means. By doing so the computational effort can be kept low. Best results were obtained using the first wave front of the first sensed signal. In this context the first sensed signal is identified by using a fixed threshold on the signal amplitude of the N channels.

According to a preferred embodiment, the acoustic signal can be sensed by at least two transforming means and the weighting of the acoustic signal can be carried out using inter-correlation products of the signals sensed by the at least two transforming means. Thus, unlike above, the directly sensed signal are not weighted but the inter-correlations are preferably used to determine the localization of an impact. Again, as for the method above, the negative impact of reflections can be suppressed without losing information from the direct signal. To even further reduce the impact of spurious contributions an inventive variant consists in weighting the sensed signals in a first step like disclosed above, and weighting the intercorrelation products in a second step.

Advantageously, the step of identifying a first wave front can comprise determining the maximum value of the inter-correlation product. As an alternative, one could also base the analysis on the maximum square amplitude, the maximum peak to peak amplitude, the root mean square etc.

These are robust parameters to identify, as a first approximation, the time difference of arrival of the signal between the two transducers for which the inter-correlation has been determined.

Preferably, the step of applying a damping window can comprise applying a symmetrical window function, in particular a Gaussian, Hamming, Hanning or Blackman window to enhance the contribution of the direct signal and to dampen the contribution of the reflections without nevertheless completely losing the content.

According to an advantageous variant, the method can further comprise applying low and/or high pass filtering to the acoustic signal which leads to a further optimization of the data from which the impact location can be derived.

The invention furthermore relates to a computer program product comprising one or more computer readable media having computer-executable instructions for performing the steps of the method of one of the preceding claims.

The object of the invention is also achieved with the device having the same advantageous effects as for the described methods.

The invention furthermore relates to a computer program product comprising one or more computer readable media having computer-executable instructions for performing the steps of the described methods.

DETAILED DESCRIPTION OF SPECIFIC EMBODIMENTS OF THE INVENTION

The present invention provides a method to treat the sensed signals to better take into account spurious contributions, like contributions from reflections at the boarder of the object. By weighting the acoustic signal, it becomes possible to keep the entire information of the signal while, at the same time, amplifying the contribution from the sensed signal which is directly received from the location of the impact with respect to contributions that may arise from reflections at the boarder of the object and which typically arrive later. As a consequence the determination of the location of the impact becomes more stable and precise In this context, it is understood that the acoustic signal which is treated is not necessarily the signal immediately sensed by transducers but can already have been treated, e.g. by an analog-to-digital transformation. According to a specific embodiment, preferably the weighting is carried out in the time domain, for which the best results have been achieved in identifying the location of an impact. According to the preferred embodiment, the signal treatment step can comprise the step of identifying a first wave front of the acoustic signal and a step of applying a damping window. The acoustic signal spreads out over the object after an impact and is sensed by a certain number of transforming means, e.g. transducers. As the first reflected contribution of a signal can only be sensed after the first wave front of the acoustic signal has already reached the transducer in question—due to geometric reasons—the identification of the first wave front is a robust parameter to identify the part of the signal which should have a higher weight factor than the rest of the sensed signal and which is taken into account by the step of applying the damping window. In this context the term "first wave front" means the part of the signal which reaches the transforming means without spurious contributions from reflections.

Preferably, the step of identifying a first wave front can comprise identifying the maximum signal amplitude, according to a specific embodiment. The maximum signal amplitude is a parameter which is easily detectable, therefore does not require extensive computational power and, at the same time, is a robust starting parameter for finding out the beginning of the acoustic signal. Instead of the maximum amplitude alternative parameters of the sensed acoustic signal could be the power of the signal, the maximum peak to peak amplitude or the energy of the signal. Prior to identify the signal amplitude a further step of signal rectification and smoothing can be carried out to facilitate the data analysis.

Figure 1:
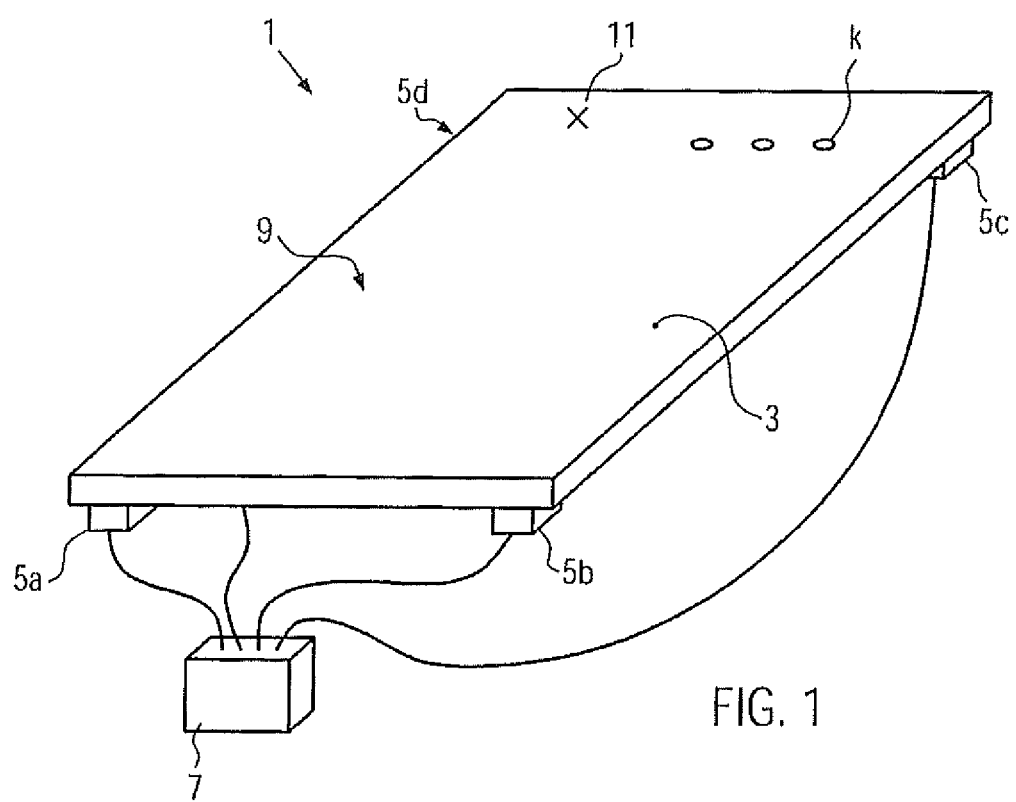
FIG. 1 is a schematic three-dimensional view of a touch-sensitive device using the method for determining the location of an impact according to the invention.

FIG. 1 is a schematic three-dimensional view of a touch-sensitive device 1 using the method for determining the location of an impact according to the invention. The touch-sensitive device 1 comprises an interaction means 3, transforming means 5a-5d (transforming means 5d is not visible in FIG. 1) and a signal processing means 7 linked to the transforming means 5a-5d.

The interaction means 3 is a transparent, semi-transparent or opaque panel which is flat or curved and can be made out of any suitable material, such as leather, latex, silicon, plastic, glass, metal, wood, plasterboard or composite material. It can be rigid or soft as long as acoustic signals can travel therein or thereon. The interaction means 3 provides a surface for allowing an interaction between a user and the device 1. In this embodiment, the user typically provides impacts on the surface side 9 which is opposite to the transforming means, nevertheless, the transforming means 5a-5d could also be arranged on the side where the impacts occur.

In FIG. 1, a touch-sensitive device 1 with four transforming means 5a-5d is illustrated. However, this number shall not be delimiting and, as long as at least two transforming means are part of the touch control system 1, the advantageous effect of the invention can be achieved. The transforming means 5a-5d comprise transducers, like strain gauges in the form of a piezoelectric transducer like ceramic or polyvinylidene fluoride (PVDF) film. Nevertheless, the transforming means 5a-5d are not limited to the use of strain gauges, as, in general, any kind of pressure or force sensor being passive or power supplied is suitable, as long as it can transform an acoustic signal generated by an impact into an electrical signal.

The transforming means 5a-5d transmit the sensed signal to the signal processing means 7 which is configured to analyse the sensed signal such that the impact location 11 can be determined. Furthermore, the processing means 7 can be configured to output the location 11 of the impact towards an additional device or trigger an action linked to the location on the object where the impact occurred.

The signal processing means 7 comprises a signal conditioning unit to adapt the sensed signals coming from the transforming means 5a-5d, for example, by filtering it, amplifying it and/or converting it into a digital signal. This signal is then further treated by the impact location unit which processes the digital signals resulting from an impact on the interaction plate 3 to determine the location (e.g. the x, y coordinates) of this impact on the interaction plate 3.

One way to determine the position of the impact will now be described:

First of all, following the impact, the four acoustic transducers 5a-5d provide sensed signals $s_i(t)$, with i from 1-4, which are then turned into discrete sensed signals $s_i(n)$ by the signal processing means 7 (the signal conditioning unit). Afterwards, a Fourier transform is carried out to obtain $S_i(w)$ for each forming means 5a-5d. The signal conditioning unit can eventually also take into account dispersion effects. Then a cross-correlation calculation is carried out: $P_{ij}=S_i(w)*S_j(w)$ on all possible combinations. The cross-correlations are re-transformed into the time domain using an inverse Fourier transform. In the next step, the various cross-correlation products are summed up $p_k(u)=\Sigma_{ij} p_{ij}(u-\tau_{ijk})$ wherein $\tau_{ijk}$ corresponds to the time difference of arrival value for a given position k on the surface of the interaction plate 3. The time difference of arrival value $\tau_{ijk}$ corresponds to difference in traveling time of the acoustic signal generated by an impact at location k with respect to the position of the transforming means i and j among the means 5a-5d. The value is either theoretically determined or at the initialization or calibration of the device 1.

Then to identify the location of impact 11, the energy maximum of $p_k(u)$ is looked for. Instead of the energy, other parameters of the cross-correlation sum can also be used, for example, the maximum value, the power or maximal square amplitude, the maximal peak to peak amplitude, the root means square etc. Further details about this method can be found in the abovementioned prior art document.

Figure 2:
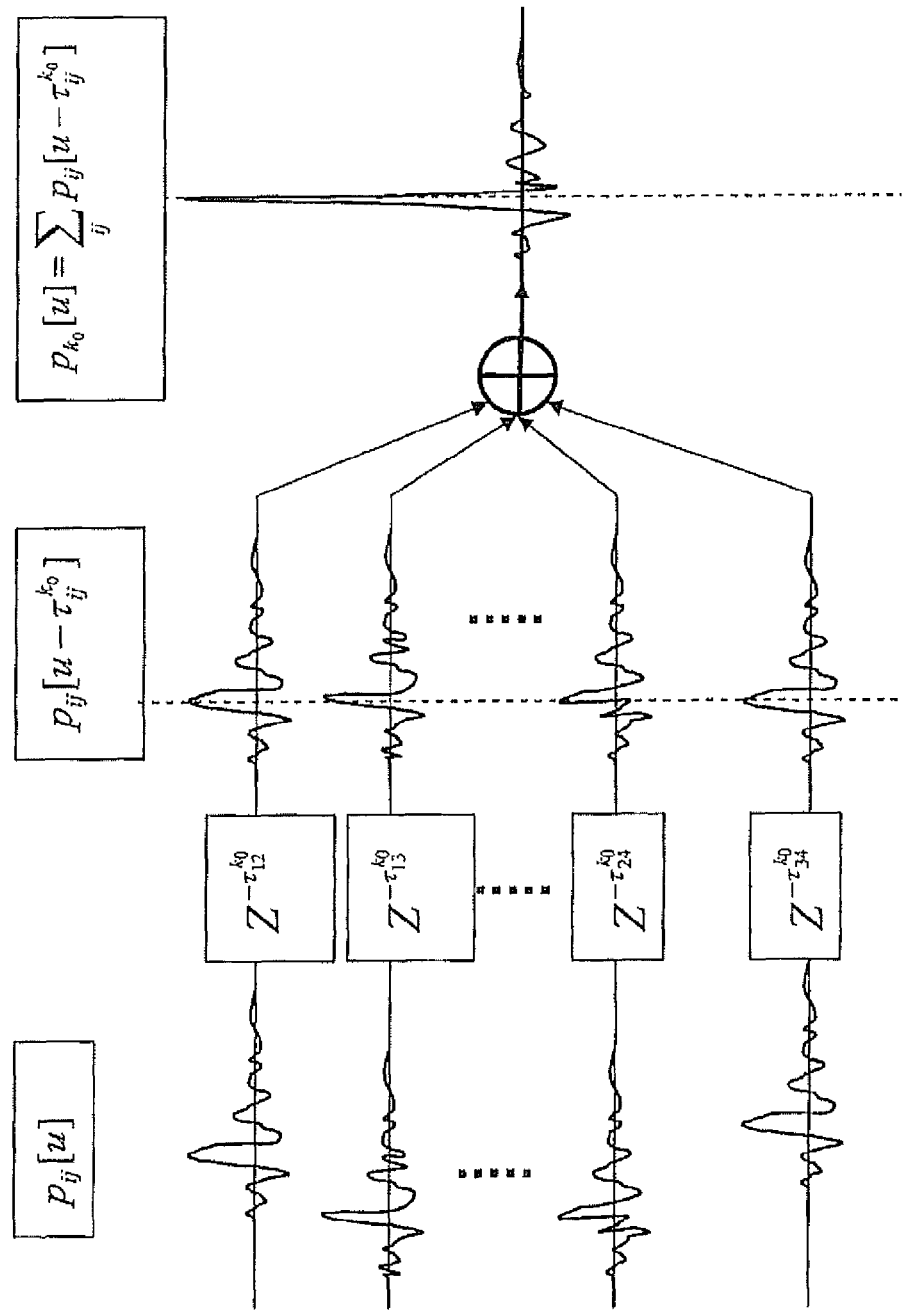
FIG. 2 illustrates cross correlation products used to determine the location of an impact.

FIG. 2 illustrates a theoretical outcome of the described method. On the left, the cross-correlation products is illustrated for a given number of transducers, in the middle the cross-correlation is corrected by the time difference of arrival value $\tau_{ijk}$ for the location $k_0$ corresponding to the location 11 of the impact and the right hand side illustrates the sum of the cross-correlation products for position $k_0$ with the expected pronounced peak.

Figure 3:
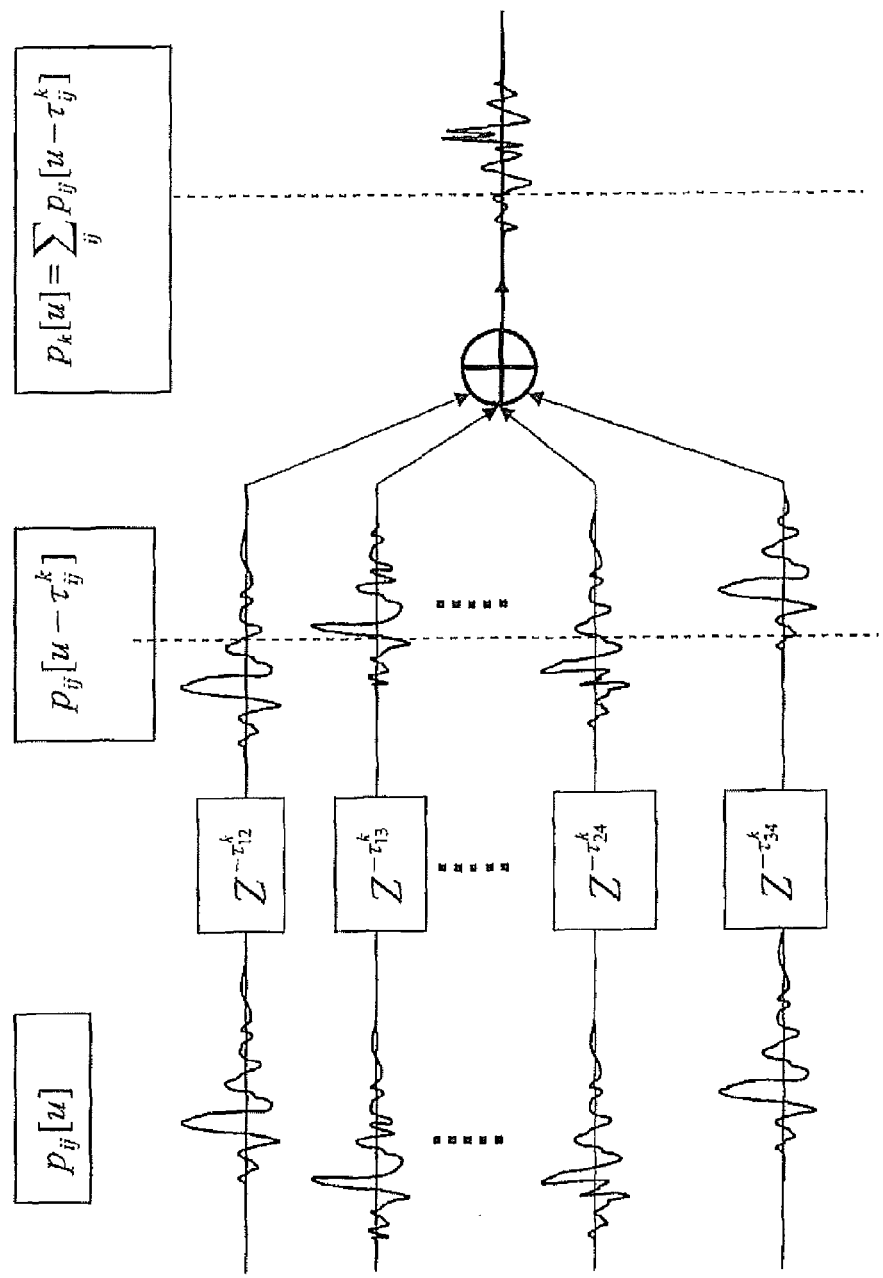
FIG. 3 illustrates the fact that the characterizing value $P_k(u)$ is low when k is different from $k_0$, where $k_0$ is the area from which the impact originated.

FIG. 3 now illustrates the characterizing value $p_k(u)$ when k does not correspond to $k_0$. In this case the characterizing value $p_k(u)$ is much lower than $p_{k0}(u)$.

Figure 4:
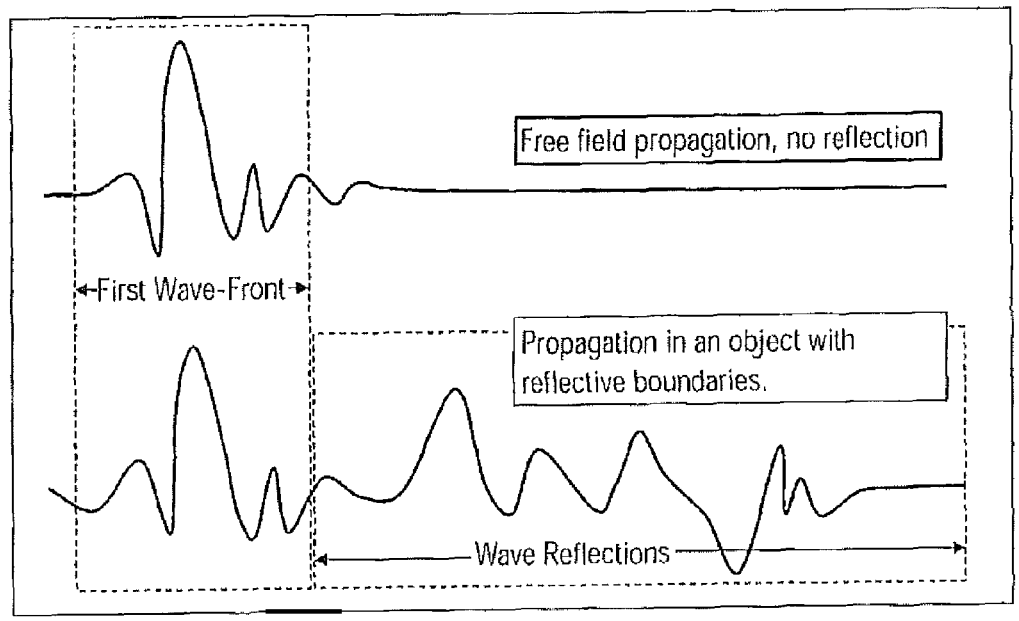
FIG. 4 illustrates the effect of reflections on an acoustic signal sensed by a transforming means.

In practice, the situation is, however, deteriorated by the presence of spurious contributions to the sensed signals, like the presence of reflections at the border of the interaction plate 3. The upper part of FIG. 4 illustrates one example of a sensed signal in the theoretical case of a free-field propagation. With no reflection the duration of the signal is limited in time. Now, in the presence of reflections due to non-perfect boundary conditions, the signal spreads out in time (lower part of FIG. 4). Like illustrated in the lower part of FIG. 4, it is no longer possible to differentiate between the first wave front which directly reaches a transforming means without reflection on the boundaries and the first contributions arising from reflections. In fact, the acoustic signal, as a consequence of the impact on the interaction plate, can already have a certain time duration so that the end of the direct sensed signal can interfere with the beginning of the reflected signal. Furthermore dispersion effects further smear out the signal.

Figure 5:
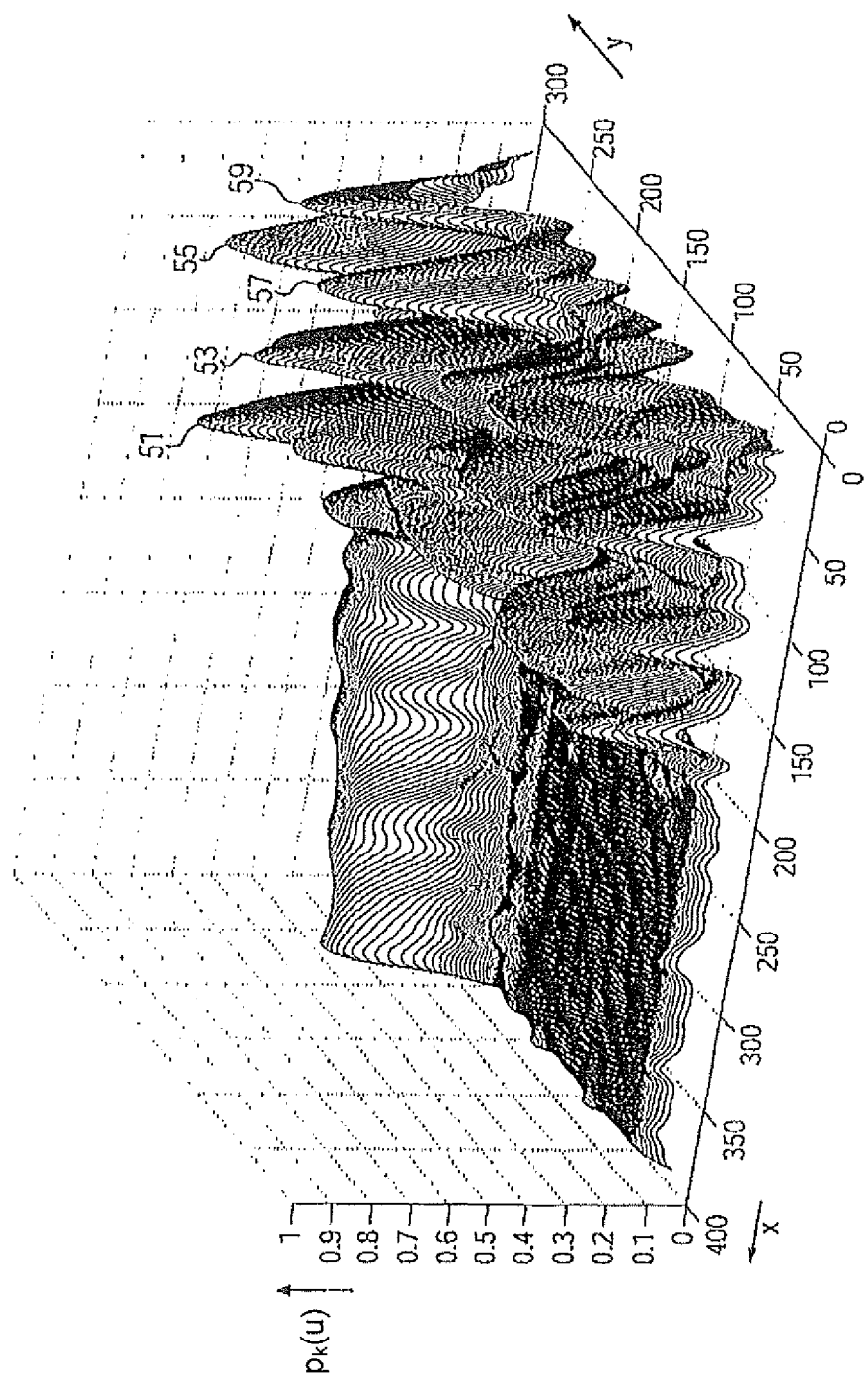
FIG. 5 illustrates the negative effect of reflections on the precision of the determination of the location of an impact.

Carrying out the method of determining the location of an impact as described above on the sensed signal comprising the spurious contributions, a result as illustrated in FIG. 5 is obtained. The three dimensional plot illustrates $p_k(u)$ as a function of the coordinates x, y of the positions k on the interaction plate 3. Due to the falsified signals, the sum of the cross-correlation product 51 corresponding to the impact location 11 has a maximum that is less pronounced compared to the one illustrated in FIG. 2. In addition, the cross correlation products of some other locations 53, 55, 57, 59 not corresponding to the real impact position $k_0$ are wrongly accentuated by the spurious contributions. Thus it becomes more difficult to identify correctly the location 11 of the impact. In the worst case, even a wrong impact location could be identified by the signal processing means 7.

To overcome this problem, the method according to the invention proposes to carry out a weighting of the sensed acoustic signals so that the contributions at the beginning have a higher impact than the signal at the end without, nevertheless, completely removing the tail of the signal. The data treatment is carried out in the signal processing means 7 either in the analogue domain, thus inside the signal conditioning unit, prior to carrying out the localization routine or in the digital domain.

This inventive signal treatment step comprises a first step of identifying a first wave front of the acoustic signal and a second step of applying a damping window. The first wave front identification is based on an estimation of the time of arrivals of the signal at each one of the transforming means 5a-5d.

The time of arrival estimation in this embodiment is achieved by, first of all, carrying out a full wave rectification and a subsequent smoothing routine by for example applying a first order low-pass filtering on the fully rectified signal. Once the signal envelope has been estimated, the maximum amplitude $A_i^{max}$ is determined for each one of the transforming means 5a-5d.

Figure 6:
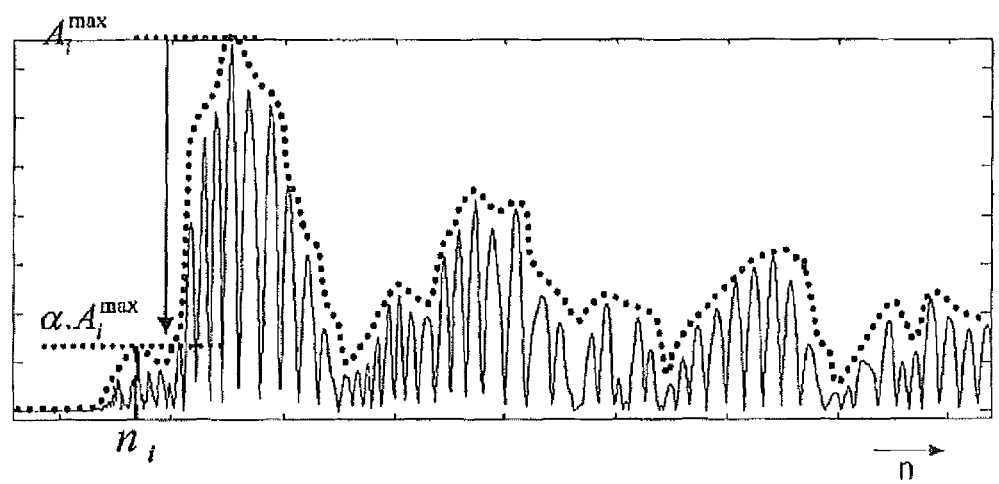
FIG. 6 illustrates a sensed signal which has been treated to identify the first wave front of the acoustic signal.

The maximum values do not necessarily correspond to the time of arrival of the first wave front; however, it has been found out that it corresponds to a robust parameter from which the time of arrival can be estimated. For this purpose it is determined when the signal first reaches a given percentage of this maximum level. This point in time is then considered to represent the time of arrival of the acoustic signal at the transforming means. Thus, the time of arrival corresponds to the time $n_i$ (in a discrete signal regime (n)) for which the signal reaches $\alpha \times A_i^{max}$ with $0<\alpha<1$. Best results have been achieved for α being in the range of 0.15 to 0.20, preferably 0.15. The described situation is illustrated in FIG. 6, showing a fully rectified and smoothed signal in which the maximum amplitude $A_i^{max}$ and the time of arrival at the time $n_i$ corresponding to $\alpha \times A_i^{max}$ is also indicated.

Figure 7:
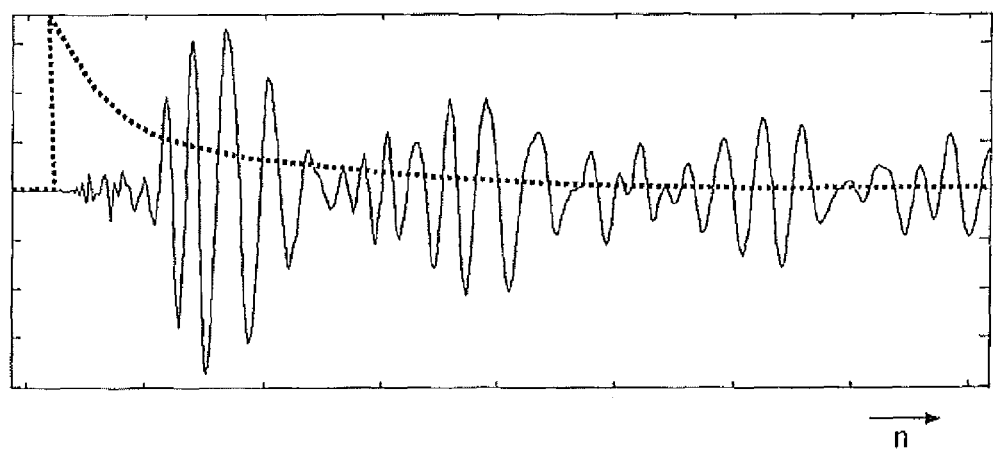
FIG. 7 illustrates the damping window used to weight the sensed acoustic signal.

The second step of applying a damping window then consists in multiplying the sensed signals with a suitable damping window, preferably an exponential window like illustrated in FIG. 7 in dotted lines. The exponential window could start with the time index $n_i$ corresponding to the time of arrival, however, best results have been achieved when the damping window starts earlier than the time of arrival. Thus, in case of an exponential window, the damping window can be defined as:

$$w(t) \begin{cases} = 0, & \text{for } 0 < t < t_i - \Delta t \\ = \exp((t_i - \Delta t - t)/T), & \text{for } t_i - \Delta t <= t, \end{cases}$$

Here $\Delta t$ corresponds to a positive value and T is the exponential time constant. For a discrete time index the equation becomes: $w(n) = \exp((n_i - \Delta n - n)/N)$. Where the discrete exponential time constant $N = T/Ts$ and where $Ts$ is the sampling period and T the exponential time constant.

As can be seen from FIG. 7, by applying the damping window, one does not just cut off the signal after a certain time duration, but information is kept over the entire signal duration.

According to a variant of this embodiment, it is possible to limit the time of arrival determination to only one of the transforming means, in particular to the one where the signal is observed first. By doing so the computational effort can be limited and the damping window can start at the same time $t_i$ or $t_i - \Delta t$ for all sensed signals.

According to a further variant, the weighting formula can also be:

$$w(t) \begin{cases} = 1, & \text{for } 0 < t < t_i - \Delta t \\ = \exp((t_i - \Delta t - t)/T), & \text{for } t_i - \Delta t <= t \end{cases}$$

In this case the beginning of the sensed signals is not cancelled.

The exponential damping window is only one inventive example, other kinds of damping windows can also be used. Indeed, any kind of damping window can be used and which is either non-symmetrical, e.g. linear, or symmetrical, e.g. Gaussian, Blackman, Hanning or Hamming. In case of a symmetrical window this could be centered around $t_i - \Delta t$. This would prevent from inadvertently cancelling the first wave front on the sensed signal.

According to a second embodiment of the invention, the method for weighting the acoustic signal is carried out on the inter-correlation product of the signals sensed by the transforming means 5a-5d as described above. In the second embodiment of the inventive method, one thus identifies the maximum value of the inter-correlation products and a damping window preferably a symmetrical one, like a Gaussian, Hamming, Hanning or Blackman window, is used to enhance the contribution of the cross-correlation which is attributed to direct signal and to damp the contribution of the signals arising from reflections.

Figure 8:
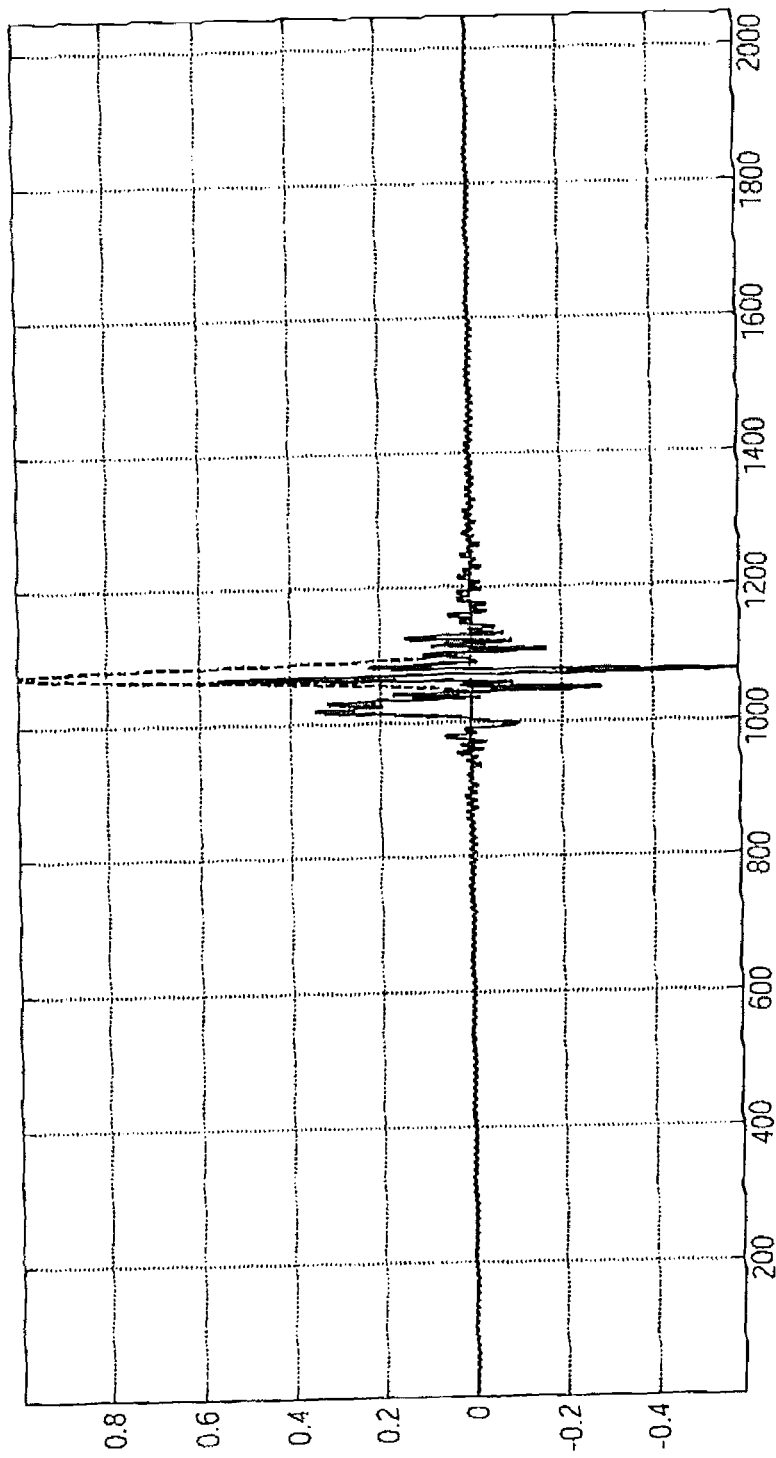
FIG. 8 illustrates the damping window used to weight intercorrelation products.

FIG. 8 illustrates the concept of this second embodiment. It shows a cross-correlation product calculated out of two sensed signals (plain line). The damping window in dotted lines is centered on the maximum of the cross-correlation product. By the way, the maximum value of the cross-correlation provides a good first approximation of the difference of time of flight of the signals of two different transforming means. The Gaussian window here is defined by $$w(n) = e^{-\frac{1}{2}\left(\frac{n-(N-1)/2}{\sigma(N-1)/2}\right)^2}, \sigma \leq 0.5$$

with $\sigma = 1e-2$ and $N = 2048$ at a sampling frequency of 44 kHz.

Figure 9:
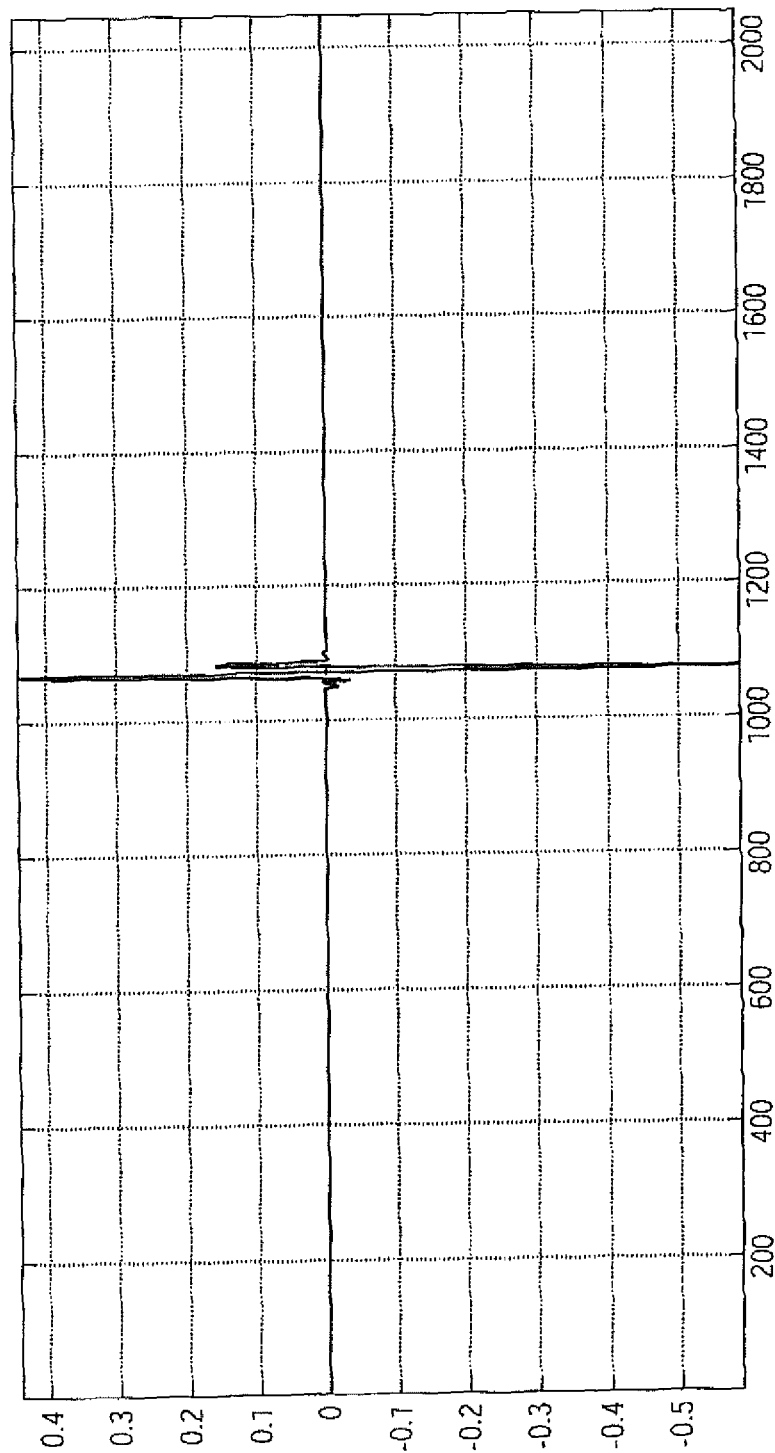
FIG. 9 illustrates the result of the weighting.

FIG. 9 illustrates the effect of the weighting of the cross correlated product which is then used to identify the location of the impact.

The first and second embodiments of the invention can also be combined to further suppress spurious contributions.

The first and second embodiments can further be improved by applying high and/or low pass filters to remove spurious contributions to the signals, e.g. arising from the power supply etc.

With the first and second embodiments according to the invention, it becomes possible to suppress, to a large extent, the negative impact of spurious contributions like arising from reflections at the boarder of the interaction means without, nevertheless, losing information necessary to determine the location of the impact.

The invention claimed is:

1. Method for determining the location of an impact on a surface of an object based on the analysis of an acoustic signal generated by the impact comprising:
   a signal treatment step of weighting the acoustic signal to thereby take into account spurious contributions in particular due to reflections at the border of the object,
   wherein the signal treatment step of weighting comprises a step of identifying a first wave front of the acoustic signal and a step of applying a damping window,
   wherein the step of applying a damping window comprises using multiplying the acoustic signal with an exponential damping window:

$$w(t) \begin{cases} = 0, & \text{for } 0 < t < t_i - \Delta t \\ = \exp((t_i - \Delta t - t)/T), & \text{for } t_i - \Delta t <= t \end{cases}$$

wherein $t_i$ corresponds to the time of arrival of the first wave front and $\Delta t$ a time delay and T is the exponential time constant.

2. Method according to claim 1, wherein the weighting is carried out in the time domain.

3. Method according to claim 1, wherein the step of identifying a first wave front comprises identifying the maximum signal amplitude.

4. Method according to claim 3, wherein the step of identifying furthermore comprises determining the arrival of the first wave front as the time when the acoustic signal passes a threshold value which is based on the maximum signal amplitude.

5. Method according to claim 1, wherein the acoustic signal is sensed by at least two transforming means and wherein the first wave front is identified for one, in particular only one, transforming means such that the same time origin of the damping window is applied for all transforming means.

6. Method according to claim 1, wherein the acoustic signal is sensed by at least two transforming means and the weighting of the acoustic signal is carried out using inter-correlation products of the signals sensed by the at least two transforming means.

7. Method according to claim 6, wherein the step of identifying the first wave fronts contribution comprises determining the maximum value of the inter-correlation product.

8. Method according to claim 6, wherein the step of applying a damping window comprises applying a symmetrical window function, in particular a Gaussian, Hamming, Hanning or Blackman window.

9. Method according to claim 1 further comprising applying low and/or high pass filtering to the acoustic signal.

10. Computer program product comprising one or more computer readable media having computer-executable instructions for performing:
   a signal treatment step of weighting the acoustic signal to thereby take into account spurious contributions in particular due to reflections at the border of the object,
   wherein the signal treatment step of weighting comprises a step of identifying a first wave front of the acoustic signal and a step of applying a damping window,
   wherein the step of applying a damping window comprises multiplying the acoustic signal with an exponential damping window:

$$w(t) \begin{cases} = 0, & \text{for } 0 < t < t_i - \Delta t \\ = \exp((t_i - \Delta t - t)/T), & \text{for } t_i - \Delta t <= t \end{cases}$$

wherein $t_i$ corresponds to the time of arrival of the first wave front and $\Delta t$ a time delay and T is the exponential time constant.

11. Device for determining the location of an impact on a surface of an object, said device arranged and configured to perform:
   a signal treatment step of weighting the acoustic signal to thereby take into account spurious contributions in particular due to reflections at the border of the object,
   wherein the signal treatment step of weighting comprises a step of identifying a first wave front of the acoustic signal and a step of applying a damping window,
   wherein the step of applying a damping window comprises multiplying the acoustic signal with an exponential damping window:

$$w(t) \begin{cases} = 0, & \text{for } 0 < t < t_i - \Delta t \\ = \exp((t_i - \Delta t - t)/T), & \text{for } t_i - \Delta t \leq t \end{cases}$$

wherein $t_i$ corresponds to the time of arrival of the first wave front and $\Delta t$ a time delay and T is the exponential time constant.

12. The computer program product according to claim 10, wherein the step of identifying a first wave front comprises identifying the maximum signal amplitude.

13. The computer program product according to claim 12, wherein the step of identifying furthermore comprises determining the arrival of the first wave front as the time when the acoustic signal passes a threshold value which is based on the maximum signal amplitude.

14. The device according to claim 11, wherein the step of identifying a first wave front comprises identifying the maximum signal amplitude.

15. The device according to claim 11, wherein the step of identifying furthermore comprises determining the arrival of the first wave front as the time when the acoustic signal passes a threshold value which is based on the maximum signal amplitude.

* * * * *

UNITED STATES PATENT AND TRADEMARK OFFICE
CERTIFICATE OF CORRECTION

| | | |
|---|---|---|
| PATENT NO. | : 8,670,290 B2 | Page 1 of 1 |
| APPLICATION NO. | : 12/991419 | |
| DATED | : March 11, 2014 | |
| INVENTOR(S) | : Aklil et al. | |

It is certified that error appears in the above-identified patent and that said Letters Patent is hereby corrected as shown below:

In the Claims:

Column 9,
Lines 13 and 14, "one or more computer readable media" should read --one or more non-transitory computer readable media--.

Signed and Sealed this
First Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,670,290 B2                                   Page 1 of 1
APPLICATION NO. : 12/991419
DATED            : March 11, 2014
INVENTOR(S)      : Aklil et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 731 days.

Signed and Sealed this

Twenty-ninth Day of September, 2015

Michelle K. Lee
*Director of the United States Patent and Trademark Office*